United States Patent [19]

Popoff et al.

[11] 4,118,378

[45] Oct. 3, 1978

[54] NON-BLOOMING ACCELERATOR AND PROCESS FOR VULCANIZATION OF EPDM ELASTOMERS

[75] Inventors: Ivan Christoff Popoff, Ambler; Everett A. Mailey, Norristown; Paul Gordon Haines, Lafayette Hill, all of Pa.

[73] Assignee: Pennwalt Corporation, Philadelphia, Pa.

[21] Appl. No.: 838,183

[22] Filed: Sep. 30, 1977

Related U.S. Application Data

[62] Division of Ser. No. 695,274, Jun. 11, 1976.

[51] Int. Cl.$^2$ .................. C08F 28/00; C08F 28/02
[52] U.S. Cl. ..................................... 526/36; 544/133; 544/137; 526/35
[58] Field of Search ................... 260/79.5 C; 544/133, 544/137

[56] References Cited

U.S. PATENT DOCUMENTS

| 3,406,171 | 10/1968 | Ghosh | 260/247.1 |
|---|---|---|---|
| 3,725,363 | 4/1973 | Albert | 260/79.5 B |
| 3,892,741 | 7/1975 | Taylor | 260/246 B |
| 3,943,143 | 3/1976 | Popoff et al. | 260/299 |
| 4,008,244 | 2/1977 | Popoff et al. | 260/306.7 R |

Primary Examiner—Ronald W. Griffin

[57] ABSTRACT

Thiuram Sulfides of oxazolidines and thiazolidines are disclosed herein and shown to be useful as non-blooming accelerators in the vulcanization of ethylene-propylene-diene-terpolymers.

25 Claims, No Drawings

NON-BLOOMING ACCELERATOR AND PROCESS FOR VULCANIZATION OF EPDM ELASTOMERS

This a division, of application Ser. No. 695,274, filed June 11, 1976.

This invention relates to new compounds found to be unexpectedly useful in the acceleration of vulcanization of elastomeric copolymers of ethylene, propylene and a diene (EPDM), and to vulcanization processes employing such compounds.

In the process of vulcanization of EPDM elastomers using an accelerator in conjunction with elemental sulfur or a sulfur-donor as a vulcanization agent, there has been a need for a non-blooming type of accelerator that has adequate activity. Some thiurams, e.g., tetramethylthiuram disulfide or tetraethylthiuram disulfide, accelerate the vulcanization reaction relatively fast but cause undesirable surface bloom on the EPDM vulcanizate. Surface bloom is a disadvantageous phenomenon characterized by the appearance of a coating of solids or oil upon the surface of a vulcanizate as a result of the migration to the surface of one or more of the compounds of the vulcanized elastomer system. The bloom renders the finished products useless for many applications in which the ozone and oxygen resistant EPDM elastomer is in demand. Such applications include coverings, linings or coatings for electrical parts, surfaces to come in contact with human or animal skin, decorative articles and the like.

EPDM elastomers are terpolymers of ethylene, propylene and a diene, e.g., 11-ethyl-1, 11-tridecadiene; 1,5-cyclooctadiene; 1,4-hexadiene; 5-ethylidene-2-norbornene; 5-methylene-2-norbornene; dicyclopentadiene; 2,5-norbornadiene; and the like. These elastomers are inherently highly blooming materials apparently due to their poor compatability with vulcanizing ingredients or with products formed during the vulcanization process. Their nature and relatively low level of unsaturation slow down the vulcanization process and require unusually highly active accelerators especially when a fast, economical rate of crosslinking is to be achieved. Recently issued U.S. Pat. No. 3,943,143 to I. C. Popoff et al. discloses and claims accelerators which provide rapid vulcanizaton of EPDM elastomers with no evidence of blooming.

The present invention provides certain new and different mono-, di-, tri- and tetrasulfides, which are fast, non-blooming accelerators for EPDM elastomers, having the following general structure:

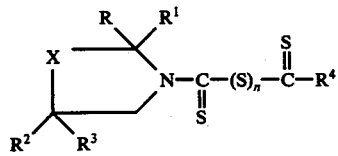

wherein R, $R^1$, $R^2$ and $R^3$ are independently selected from the group consisting of hydrogen, alkyl and chloralkyl radicals each having from 1 to 17 carbon atoms, alkenyl radicals having from 2 to 17 carbon atoms, phenyl, naphthyl, substituted phenyl and substituted naphthyl radicals each having substituents selected from the group consisting of Cl, OH, $OR^5$ and $NR^5 R^6$ wherein $R^5$ and $R^6$ are alkyl radicals having 1 to 8 carbon atoms, and $n$ is an integer of from 1 to 4; $R^4$ is selected from the group consisiting of:

(a) $-NR^7 R^8$ wherein $R^7$ and $R^8$ are the same or different alkyl radicals having from 1 to 18 carbon atoms and together having a total of at least 5 carbon atoms;

(b) $-NZ$ wherein N is the ring nitrogen atom of a cyclic amine and Z represents that portion of the cyclic amine ring having at least 5 ring carbon atoms one of which can be replaced by an oxygen or sulfur atom; and

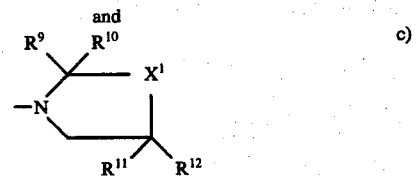

wherein $R^9$, $R^{10}$, $R^{11}$ and $R^{12}$ are independently selected from the same group from which R is selected and at least one of $R^9$, $R^{10}$, $R^{11}$ and $R^{12}$ is other than hydrogen; and X and $X^1$ in the above structures are oxygen or sulfur.

In preferred embodiments of the compounds of this invention when R, $R^1$, $R^2$, $R^3$, $R^9$, $R^{10}$, $R^{11}$, and $R^{12}$ are alkyl they are methyl; when alkenyl they are 1-ethylpentenyl-1; when chloralkyl they are trichloromethyl; when substituted phenyl or substituted naphthyl they have no more than two substituent groups on any one phenyl or naphthyl ring structure; when phenyl, naphthyl, substituted phenyl or substituted naphthyl, only one such aryl group will be attached to the same oxazolidine or thiazolidine ring carbon atom; and when $R^4$ is $-NZ$, $-NZ$ represents a morpholino or piperidino ring structure.

$R^7$ and $R^8$ are independently selected from alkyl radicals including for example, ethyl, butyl, hexyl, octyl, decyl, dodecyl, hexadecyl and octadecyl radicals. Preferably, at least one of $R^7$ and $R^8$ is butyl, octyl or octadecyl.

A convenient method of preparing the thiuram di-, tri- and tetrasulfides of this invention is to provide the corresponding tri (lower alkyl) ammonium oxazolidine- or thiazolidinecarbodithioate, for example, by a procedure as set forth in the aforementioned U.S. Pat. No. 3,943,143. This carbodithioate is then reacted in the appropriate solvent medium with an appropriate sulfur compound, i.e., $SCl_2$ or $S_2Cl_2$, supplying the additional sulfur for the desired tri- or tetra sulfide. The thiuram disulfides are obtained by the oxidation of the appropriate carbodithioate. After filtration, solvent removal and purification, the product is ready for use as an accelerator for the vulcanization of EPDM elastomers. The thiuram monosulfide is readily prepared by first providing the corresponding disulfide in the manner generally described above and then reacting this product with a compound capable of removing one of the sulfur atoms of the disulfide moiety of the product, e.g. sodium cyanide. Another method is by the reaction of a carbodithioate with the appropriate thiocarbamoyl chloride.

As previsouly stated, the compounds of this invention are used as accelerators in conjunction with sulfur or a sulfur donor as a vulcanization agent for EPDM elastomers to very rapidly provide a vulcanized product showing no evidence of blooming. Examples of their preparation and the preparation of similar compounds produced for comparison purposes, as well as the results found when using these compounds as vulcanization accelerators, are set forth as follows:

EXAMPLE 1

Preparation of Bis (N,N-diethylthiocarbamoyl) Sulfide

Compound was prepared according to the procedure of J. J. D'Amico et al., Rubber Chem. and Tech., 41(3), 718 (1968) in 75% conversion, $n^{25}$ D 1.6177.

Calculated for $C_{10}H_{20}N_2S_3$: N, 10.59 Analyzed and found N, 10.86

EXAMPLE 2

Preparation of Bis (N-cyclohexyl-N-ethylthiocarbamoyl)Disulfide

To a one liter flask was added 127g (1.0 mole) of N-ethyl-N-cyclohexylamine and 80g (1.0 mole) of a 50% aqueous sodium hydroxide solution. To the mixture, maintained at 20°–21°, was added 76g (1.0 mole) of carbon disulfide. Sufficient water was then added upon the completion of the feed to dissolve all of the sodium N-ethyl-N-cylcohexyldithiocarbamate. The resulting solution was stirred an additional 30 minutes.

To the above solution was added 5.0g of hydrogen peroxide as a 30% solution over a period of five minutes, and then a solution of 51.7g (0.5 mole total) of 98% sulfuric acid over a period of 2.75 hours at a temperature of 17°–25°. After the mixture was stirred an additional hour at ambient temperatures, the contents of the flask were transferred to a separatory funnel. After the bottom, aqueous layer was removed and discarded, the top layer was diluted with 300ml of benzene. The organic phase was washed with 10 × 200 ml of water, was dried and then was removed of volatiles at 25° at 1mm Hg to yield the desired product, a viscous, dark amber liquid (157 g, 78% conversion).

Calculated for $C_{18}H_{32}N_2S_4$ N, 6.92 Analyzed and found N, 7.02

EXAMPLE 3

Preparation of Thiuram Disulfides from N-Carbodithioates of Diethylamine and 2-Trichloromethyloxazolidine To a stirred solution of 55.5 g (0.15 mole) triethylammonium 2-trichloromethyl-3-oxazolidinecarbodithioate and 34.5 g (0.15 mole) of sodium diethyldithiocarbamate of 74.5% purity in 9 l. water was added 48.5 g (0.18 mole) potassium persulfate at ambient temperature over a 30 minute period. The resultant water-oil mixture was stirred an additional four hours, afterwhich the water was decanted and the oil was dissolved in methylene chloride. The organic layer was washed with 2 l. (10×200 ml) water, dried with magnesium sulfate and filtered. After the voatiles were removed under reduced pressure, 56g (90% conversion) of pale amber liquid product was obtained.

Calculated for $C_{10}H_{15}Cl_3N_2OS_4$(avg): C, 29.02; H, 3,65; N, 6.77 Analyzed and found C, 28,57; H, 3.30; N, 6.30

EXAMPLE 4

Preparation of Diethylthiocarbamoyl (2-Trichloromethyloxazolidino) thiocarbonyl Sulfide A solution of 52.2 g (0.15mole) triethylammonium 2-trichloromethyl-3-oxazolidinecarbodithioate and 22.7g (0.15 mole) of diethylthiocarbamoyl chloride in 3.5 l. of dry acetone was stirred first at ambient temperature for six hours and then at 50° for 5.5 hours. After filtering off the solids, the resulting filtrate was evaporated under reduced pressure to yield a yellow mixture which was washed with water. The residue after washing was taken up in benzene and washed additionally with water. The organic layer was dried with magnesium sulfate; the mixture was filtered; the filtrate was evaporated under reduced pressure to yield an oil. The oil was extracted with (10×100 ml) isopropanol and the combined extracts were chilled to 0° C., the resulting solids were filtered off to yield 23 g (40% conversion) of the desired yellow solid product, m.p. 69°–70°.

Calculated for $C_{10}H_{15}Cl_3N_2OS_3$: C, 31.46; H, 3.95; N, 7.34 Analyzed and found C, 31.34; H, 4.16; N, 7.42

EXAMPLE 5

Preparation of Thiuram Disulfides from N-Carbodithioates of Diethylamine and Thiazolidine A solution of 24.1g (0.097 mole) ammonium persulfate in 100 ml water was added to a solution of 20.2g (0.088 mole) sodium diethyldithiocarbamate containing 25% water and 23.4g (0.088 mole) triethylammonium, 3-thiazolidinecarbodithioate in 500 ml water at 20°–5° over a period of 25 minutes. The mixture was stirred an additional four hours and then was filtered. After washing the solid in a Waring Blendor with 250 ml water, filtering and air-drying, 25.7g (94% conversion) of pale yellow product was obtained, m:p. 55°–120°. It is a mixture of three products, i.e., tetraethylthiuram disulfide, bis (thiazolidinothiocarbonyl) disulfide, and diethylthiocarbamoyl thiazolidinothiocarbonyl disulfide.

Calculated for $C_9H_{16}N_2S_5$: C. 34.6; N, 5.16; N, 8.97; S, 51.2 Analyzed and found C, 34.6; H, 5.13; N, 8.73; S, 51.0

EXAMPLE 6

Preparation of Diethylthiocarbamoyl Oxazolidinothiocarbonyl Sulfide

To a solution of 37.5g (0.15 mole) triethylammonium 3-oxazolidinecarbodithioate in 200 ml methylene chloride was added 22.7g (0.15 mole) diethylthiocarbamoyl chloride in 100 ml methylene chloride at 22°–6° over a period of 40 minutes. After refluxing for 4 hours, the solution was cooled to 25°, washed with 7×500 ml water and then removed of volatiles under reduced pressures. The resulting mixture was extracted with 7 × 50 ml ether. The ethereal solution was washed with 20% aqueous sodium hydroxide solution followed by water washing (3×100 ml). After drying with magnesium sulfate and filtering off the solids, the solution was removed of volatiles under reduced pressures to give 24g (61% conversion) of clear dark amber oil, $n_D^{25}$ 1.6647

Calcuated for $C_9H_{16}N_2OS_3$: C, 40.9; H, 6.10; N, 10.6 Analyzed and found C, 40.4; H, 6.00; N, 9.67

EXAMPLE 7

Preparation of Dimethylaminothiocarbonyl Thiazolidinothiocarbonyl Sulfide

A solution of 34.6 g (0.280 mole) diemthylthiocarbamyl chloride in 100 ml methylene chloride was refluxed for 2 hours with a solution of 75.0 g (0.282 mole) triethylammonium 2-trichloromethyloxazolidine-3-carbodithioate in 300 ml methylene chloride. At room temperature, 200 ml water was stirred in. The organic layer (bottom) was separated and washed five times with 100-ml portions of 10% sodium hydroxide solution and then with 100-ml portions of water until the washes were neutral to pH paper. The organic layer was dried with anhydrous magnesium sulfate. The drying agent was filtered off and the filtrate was vacuum-stripped to leave a residue of 50.2g slurry of crystals and oil (71% yield). The slurry was pressed on a porous plate. The resulting crystalline residue was thoroughly washed with hexane to leave yellow crystals, m. 67°–70° C. Its infrared spectrum confirmed the expected structure.

Calculated for $C_7H_{12}N_2S_4$: C. 33.33; H, 4.76; N. 11.11 Analyzed and found C, 33.30; H, 4,72; N, 11.10

EXAMPLE 8

Preparation of Bis (oxazolidinothiocarbonyl) Sulfide

A solution of 41.4g. (0.14 mole) bis (oxazolidinothiocarbonyl) disulfide in 1750 ml acetone and 8.2g (0.17 mole) sodium cyanide in 50 ml water was stirred first at ambient temperatures for 30 minutes and then a at 45° for 15 minutes. The mixture was removed of volatiles at ambient temperatures and one mm Hg to yield a dark semi-solid which was extracted with 500 ml (10 × 50 ml) benzene. The benzene extract was then washed with water and was dried with magnesium sulfate. After the resulting mixture was filtered and the filtrate was removed of volatiles under reduced pressures, the remaining solid was washed with ether to yield 19g (48% conversion) of the expected yellow product, m.p. 112°–115°.

Calculated for $C_8H_{12}N_2O_2S_3$: C, 36.4; H, 4.58; N, 10.6; S, 36.3 Analyzed and found C, 36.6; H, 4.39; N, 10.2; S, 36.3

EXAMPLE 9

Preparation of Bis (oxazolidinothiocarbonyl) Disulfide

To a solution of 150g (0.6 mole) triethylammonium 3-oxazolidinecarbodithioate in 200 ml water was added 81.1g (0.3 mole) potassium persulfate in 500 ml water at 2°–7° over a period of 40 minutes during which time solids were formed. The precipitate was filtered, washed in a Waring Blendor with cold water (5 × 500 ml), filtered each time, and air-dried to yield 66g (37% conversion) of white solid product, m.p. 103°–5°. A sample, m.p. 110°–1°, obtained by reprecipitation from benzene-ether solution and still slightly contaminated, was analyzed. Its infrared spectrum confirmed the expected structure.

Calculated for $C_8H_{12}N_2O_2S_4$: C, 32.4; H, 4.08; N, 9.46 Analyzed and found C, 31.1; H, 3.92; N, 8.75

EXAMPLE 10

Preparation of Bis (oxazolidinothiocarbonyl) Tetrasulfide

To a solution of 50.0g (0.2 mole) triethylammonium 3-oxazolidinecarbodithioate in 200 ml methylene chloride was added a solution of 13.5g (0.1 mole) sulfur monochloride in 25ml methylene chloride over a period of 20 minutes and at −4° to −6°. The mixture, after being stirred 30 minutes at −6° to 0° and then at ambient temperatures for two hours, was filtered and the resulting filtrate was evaporated to dryness under reduced pressures. The yellow residue was washed with 4 × 150 ml water in a Waring Blendor to yield after air-drying and washing with ether, 23g (64% conversion) of cream-colored solid product, m.p. 99°–107°.

Calculated for $C_8H_{12}N_2O_2S_6$: N, 8.78; S, 48.2 Analyzed and found N, 8.21; S, 48.2

EXAMPLE 11

Preparation of Bis[(2-trichloromethyloxazolidino)thiocarbonyl]Disulfide

To a solution of 73.6g (0.2 mole) triethylammonium 2-trichloromethyl-3-oxazolidinecarbodithioate in 1000 ml water and 100 ml methanol at 35° was added 32.4g (0.12 L mole) potassium persulfate in 400 ml water over a period of 20 minutes. After being stirred at ambient temperatures for 19 hours, the solids were filtered, washed with 1.8 l. (6×300 ml) water and air-dried to yield 48g (90% conversion) of cream-colored product, m.p. 158°–161° C. A small samples was recrystallized from benzene, m. p. 170°–1°.

Calculated for $C_{10}H_{10}Cl_6N_2O_2S_4$: C, 22.62; H, 1.90; N, 5.27; S, 24.20 Analyzed and found: C, 22,87; H, 1.98; N, 5.12; S, 23.31

EXAMPLE 12

Preparation of Bis[(2-trichloromethyloxazolidino) thiocarbonyl]Sulfide

To a solution of 48.0g (0.09 mole) bis[(2-trichloromethyloxazolidino)thiocarbonyl]disulfide in 1.7 l. acetone (warmed slightly to dissolve the disulfide and then cooled to ambient temperatures) was added 5.3g (0.108 mole) sodium cyanide in 50 ml water. The solution was stirred an additional 30 minutes at ambient temperatures and then 15 minutes at 58°. After the volatiles were removed under reduced pressure, the resulting solids were washed with water (4×400 ml) and then were air dried. These solids were washed with hexane to yield 31g (69% conversion) of yellow solid product, m.p. 131°–5° (gas evol.).

Calculated for $C_{10}H_{10}Cl_6N_2O_2S_3$: C, 24.05; H, 2.01; N, 5.61; S, 19.23 Analyzed and found C, 24.59; H, 2.10; N, 5.84; S, 18.83

EXAMPLE 13

Preparation of Bis[(2-trichloromethyloxazolidino)thiocarbonyl]Trisulfide

To 86.3g (0.24 mole) Triethylammonium 2-trichloromethyl-3-oxazolidinecarbodithioate in 400 ml methylene chloride, cooled to −10° C. was added a solution of 12.3g (0.12 mole) sulfur dichloride in 75 ml methylene chloride over a period of 40 minutes. Stirring of the turbid amber mixture was continued for an additional 4 hours with no external cooling. The mixture was filtered, and the filtrate was evaporated under reduced pressure; the resulting solids were washed with 3.51(7×500 ml) water and were air dried to yield 62.5g (56% conversion) of the desired yellow solid product, m.p. 137°–48°.

Calculated for $C_{10}H_{10}Cl_6N_2O_2S_5$: C, 21.32; H, 1.79; N, 4.98; S, 28.41 Analyzed and found C, 21.40; H, 2.00; N, 4.84; S, 28.79

EXAMPLE 14

Preparation of Bis[(2-trichloromethyloxazolidino)thiocarbonyl]Tetrasulfide

To 220.8g (0.6 mole) triethylammonium 2-trichloromethyl-3-oxazolidinecarbodithioate in 750 ml methylene chloride at −10° was added a solution of 40.5g (0.3 mole) sulfur monochloride in 50 ml methylene chloride over a period of 40 minutes. The mixture was stirred at ambient temperatures for an additional 5 hours and then was filtered. The filtrate was evaporated to dryness under reduced pressures to yield a solid which was washed in a Waring Blendor with 5 × 250 ml water and then air-dried to obtain 140.5g (78% conversion) of the desired yellow solid product, m.p. 144°–55°.

Calculated for $C_{10}H_{10}Cl_6N_2O_2S_6$: C, 20.15; H, 1.81; N, 4.70; S, 32.22 Analyzed and found C, 19.54; H, 1.80; N, 4,80; S, 35.71

EXAMPLE 15

Preparation of Bis[(2-phenyloxazolidino)thiocarbonyl]Disulfide

To a solution of 155g (0.5 mole) triethylammonium 2-phenyl-3-oxazolidinecarbodithioate in 1.5 l. water was added a solution of 67g (0.25 mole) potassium persulfate in 1.4 l. water at 18°–22° in 2.75 hours. The resulting mixture was stirred an additional hour and then was filtered. The solid was washed with water twice in a Waring Blendor and then was air-dried to yield 100g (88% yield) of the expected white solid product, m.p. 158°–61°.

Calcuated for $C_{20}H_{20}N_2O_2S_4$: C, 53.6; H, 4.50; N, 6.25; S, 28.6 Analyzed and found C, 53.1; H, 4.72; N, 6.06; S, 28.4

EXAMPLE 16

Preparation of Bis[(2-trichloromethylthiazolidino)thiocarbonyl]Disulfide

A solution of 65.3g (0.286 mole) ammonium persulfate in 200 ml water was added to 99.7g (0.26 mole) triethylammonium 2-trichloromethyl-3-thiazolidinecarbodithioate in 3 l. water at 22°–3° over a period of 50 minutes. After the yellow slurry had stirred at ambient temperatures an additional 16 hours, it was filtered to give a solid which was washed with 2 × 1 l. water in a Waring Blendor. The resulting yellow solid product, after air-drying weighed 61g (83% conversion), m.p. 140.5°–1.0° (gas evol.).

Calculated for $C_{10}H_{10}Cl_6N_2S_6$: C, 21.3; H, 1.79; N, 4.98; S, 34.1 Analyzed and found C, 22.0; H, 2.00; N, 5.09; S, 33.3

EXAMPLE 17

Preparation of Bis[(2-trichloromethylthiazolidino)thiocarbonyl]Trisulfide

To a solution of 49.7g (0.13 mole) triethylammonium 2-trichloromethyl-3-thiazolidinecarbodithioate in 300 ml methylene chloride was added 6.7g (0.065 mole) sulfur dichloride in 50 ml methylene chloride. The addition was made at −5 to −9° over a period of 10 minutes during which time solids formed. The mixture was refluxed for four hours, after which time it was cooled and washed with cold (5°) water (5 × 500 ml). The organic layer was dried with magnesium sulfate, the salt filtered off and the resulting filtrate evaporated under reduced pressure to give 35.8g (92% conversion) of the expected yellow solid product, m.p. 140°–192°.

Calculated for $C_{10}H_{10}Cl_6N_2S_7$: C, 20.2; H, 1.69; N, 4.71; S, 37.6 Analyzed and found C, 20.2; H, 1.86; N, 4.38; S, 36.9

EXAMPLE 18

Preparation of Bis[(2-trichloromethylthiazolidino)thiocarbonyl]Tetrasulfide

To a solution of 38.4g (0.10 mole) triethylammonium 2-trichloromethyl-3-thiazolidinecarbodithioate in 500 ml methylene chloride was added a solution of 6.8g (0.05 mole) sulfur monochloride in 50 ml methylene chloride at −5° over a period of 30 minutes. After stirring an additional 18 hours at ambient temperatures, the solution was evaporated under reduced pressure to give a solid residue which was washed twice in a Waring Blendor and then air-dried to yield 21g (67% conversion) of yellow product, m.p. 60°–75°.

Calculated for $C_{10}H_{10}Cl_6N_2S_8$: C, 19.2; H, 1.61; N, 4.47 Analyzed and found C, 19.2; H, 1.88; N, 4.31

EXAMPLE 19

Preparation of Thiuram Disulfides from N-Carbodithioates of Dibutylamine and 2-trichloromethyloxazolidine To the sodium dibutyldithiocarbamate solution prepared from 7.1g (0.055 mole) dibutylamine, 4.6g (0.06 mole) carbon disulfide, 4.4g (0.055 mole) of 50% aqueous sodium hydroxide and 200 ml water, was added a solution of 18.4g (0.05 mole) triethylammonium 2-trichloromethyl3-oxazolidinecarbodithioate in 2 l. water. Potassium persulfate (13.5g, 0.05 mole) in 250 ml water was added to the above solution in 10 minutes at 25°. Stirring was continued an additional two hours during which time a semi-solid was formed. The reaction mixture was chilled to 5° and then was filtered. The plastic solid was then taken up in benzene and washed additionally with water (10×200 ml). After the organic layer was separated, dried with magnesium sulfate and filtered, the solvent was removed under reduced pressures to yield 21g (89% conversion) of yellow semisolid. It is a mixture of three products, i.e., tetrabutylthiuram disulfide, bis[(2-trichloromethyloxazolidino)thiocarbonyl]disulfide, and dibutylthiocarbamoyl (2-trichloromethyloxazolidino)-thiocarbonyl disulfide.

Calculated for $C_{14}H_{23}Cl_3N_2OS_4$(average): N, 5.96; S, 27.2 Analyzed and found N, 5.61; S, 26.8

EXAMPLE 20

Preparation of Thiuram Disulfides from N-Carbodithioates of Dibutylamine and 2-Trichloromethylthiazolidine To a solution of sodium dibutyldithiocarbamate [prepared from 7.1g (0.55 mole) dibutylamine, 4.6g (0.06 mole) carbon disulfide, 4.4g (0.55 mole) as 50% aqueous sodium hydroxide, and 200 ml water] 19.2g (0.05 mole) triethylammonium 2-trichloro methyl-3-thiazolidinecarbodithioate and 3.5 l water was added a solution of 11.4g (0.04 mole) ammonium persulfate at 24° over a period of 25 minutes. After stirring an additional 2.5 hours at ambient temperatures, 400 ml methylene chloride was added to give two liquid layers. After the organic layer was separated, washed with 15 × 250 ml water, dried and removed of volatiles under reduced pressures, 22g (90% conversion) of dark amber oil was obtained. The oil becomes semi-solid on standing. This product is a mixture of tetrabutylthiuram disulfide, dibutylthiocarbamoyl(2-trichloromethylthiazolidine)-thiocarbonyl disulfide and bis[(2-trichloromethylthiazolidino) thiocarbonyl]disulfide.

Calculated for $C_{14}H_{23}Cl_3N_2S_5$ (average) C, 34.6; H, 4.77; N, 5.77; Analyzed and found C, 35.3; H, 5.10; N, 5.69;

EXAMPLE 21

Preparation of Dibutylthiocarbamoyl (2-Phenyloxazolidino)thiocarbonyl Sulfide

To a solution of 29.9g (0.26 mole) thiophosgene in 600 ml ethyl ether at 0° was added a solution of 25.8g (0.20 mole) dibutylamine 20.2g (0.20 mole) triethylamine and 250 ml ethyl ether over a period of 35 minutes during which time solids formed. After stirring an additional one hour, the mixture was filtered and the resulting filtrate was removed of volatiles under reduced pressures to yield 35g of crude dibutylthiocarbamoyl chloride.

A solution of the above 35g thiocarbamoyl chloride in 50 ml methylene chloride was added to a solution of 52.7g (0.17 mole) triethylammonium 2-phenyl-3-oxazolidinecarbodithioate and 200 ml methylene chloride at 20°-3°. During the 30 minute addition time, solids formed. After the contents of the flask were heated at 42° for two hours, the mixture was cooled to 25°, 250 ml methylene chloride was added and the resulting mixture was washed with 3 × 300 ml water, 3 × 100 ml of 20% aqueous sodium hydroxide, and finally with 2 × 300 ml water. The organic layer was dried with magnesium sulfate, removed of solids by filtration and of solvent by distillation to yield 62g (92% conversion) of the desired dark amber, viscous crude product. Its structure was confirmed by infrared analysis.

Calculated for $C_{19}H_{28}N_2OS_3$: N, 7.07; S, 24.2; Analyzed and found N, 6.23; S, 22.6;

EXAMPLE 22

Preparation of Thiuram Disulfides from N-Carbodithioates of 2-Trichloromethyloxazolidine and 2-Trichloromethylthiazolidine To a mixture of 29.4g (0.08 mole) triethylammonium 2-trichloromethyl-3-oxazolidinecarbodithioate and 30.7g (0.08 mole) triethylammonium 2-trichloromethyl-3-thiazolidinecarbodithioate in 2 l. of water was added a solution of 18.2g (0.07 mole) ammonium persulfate in 200 ml of water. The addition was made at 23° over a period of 35 minutes after which time the mixture was stirred an additional two hours at ambient temperatures. The solids were filtered, washed in a Waring Blendor with (4×1.5 l.) of water and air-dried to give 44.5g (100% conversion) of the desired product, m.p. 139°-41°. It is a mixture of bis[(2-trichloromethyloxazolidino)thiocarbonyl] disulfide, bis[(2-trichloromethylthiazolidino)thiocarbonyl]disulfide and (2-trichloromethyloxazolidino) thiocarbonyl (2-trichloromethylthiazolidino)thiocarbonyl disulfide.

Calculated for $C_{10}H_{10}Cl_6N_2OS_5$ (average): C, 22.0; H, 1.84; N, 5.12; S, 29.2 Analyzed and found C, 22.5; H, 2.07; N, 5.33; S, 29.3

EXAMPLE 23

Preparation of Bis[(2-trichloromethylthiazolidino)thiocarbonyl]Sulfide

A solution of 4.1g (0.084 mole) sodium cyanide in 50 ml water was added to a mixture of 45.1g (0.08 mole) bis[(2-trichloromethylthiazolidino)thiocarbonyl] disulfide and 1400 ml acetone at 21° over a period of 15 minutes. All solids had dissolved after the cyanide addition; then the solution was stirred 30 minutes at 21°-4°. Solids began appearing during this time. After the mixture was stirred an additional 15 minutes at 40°-5°, then cooled to 25°, the solids were filtered (filtrate set aside) to give 11.5g (24% conversion) yellow solid product, m.p. 197°-9°.

Calculated for $C_{10}H_{10}Cl_6N_2S_5$: C, 22.6; H, 1.90; Cl, 40.0; N, 5.27; S, 30.1 Analyzed and found C, 22.8; H, 1.98; Cl, 39.8; N, 5.38; S, 30.0

EXAMPLE 24

Preparation of Dibutylthiocarbamoyl Thiazolidinothiocarbonyl Sulfide

To a solution of 29.9g (0.26 mole) thiophosgene in 600 ml ethyl ether was added a solution of 25.8g (0.2 mole) dibutylamine and 20.2g (0.2 mole) triethylamine in 250 ml ethyl ether at 0° over a period of 35 minutes. After stirring an additional one hour with no external cooling, the mixture was filtered and the resulting filtrate was removed of volatiles under reduced pressures. To remove the last traces of thiophosgene from the crude dibutylthiocarbamoyl chloride, the residue was taken up in 300 ml hexane and again removed of solvent under reduced pressures.

A solution of the above thiocarbamoyl chloride in 50 ml methylene chloride was added to a solution of 71.8g (0.187 mole) triethylammonium 2-trichloromethyl-3-thiazolidinecarbodithioate in 250 ml methylene chloride at 20°-5° in 30 minutes. The mixture was heated at 39°-51° for 3 hours and then washed at ambient temperatures with 2×400 ml water, 3×100 ml 10% aqueous sodium hydroxide and again with 5×400 ml water. After drying the organic layer and removing the solvent under reduced pressures, 75g (88% conversion) of the desired amber-colored liquid product was obtained.

Calculated for $C_{14}H_{23}Cl_3N_2S_4$: C, 37.0; H, 5.11; N, 6.17; Analyzed and found C, 36.2; N, 4.86; N, 5.99

EXAMPLE 25

Preparation of Bis[(5-phenyloxazolidino)thiocarbonyl]Disulfide

To a solution of 64.0 g (0.196 mole) triethylammonium 5-phenyl-3-oxazolidinecarbodithioate in 1.8 l. water was added a solution of 23.9g (0.105 mole) ammonium persulfate in 240 ml water at 24°-6° over a period of 20 minutes. After stirring at ambient temperatures for 19 hours, the mixture was filtered and the solids were washed with 8×400 ml water in a Waring Blendor and then air-dried to yield 40g (92% conversion) of the desired white, solid product m.p. 116°-23°.

Calculated for $C_{20}H_{20}N_2O_2S_4$: C, 53.6; H, 4.50; N, 6.25 Analyzed and found C, 53.2; H, 4.80; N, 6.31

EXAMPLE 26

Preparation of (2-Trichloromethyloxazolidino)thiocarbonyl (2-Trichloromethylthiazolidino) thiocarbonyl Sulfide A sample of (2-trichloromethyloxazolidino)thiocarbonyl chloride was prepared by adding a solution of 19g (0.1 mole) 2-trichloromethyloxazolidine, 10.1g (0.1 mole) triethylamine and 150 ml ethyl ether to a solution of 14.9 g (0.13 mole) thiophosgene and 400 ml ethyl ether at 0° over a period of 30 minutes. After stirring with no external cooling for one hour, the mixture was filtered, the resulting filtrate was removed of solvent under reduced pressures and was washed with hexane to yield 16.1g (60% conversion) of tan, solid thiocarbamoyl chloride, m.p. 97°–9°.

The above carbamoyl chloride in 50 ml methylene chloride was added to a solution of 23.0 g triethyl ammonium-2-trichloromethyl-3-thiazolidinecarbodithioate and 400 ml methylene chloride at 21° over a period of 10 minutes. After stirring at ambient temperatures for 1.5 hours, the solution was heated at 39°–41° for 5 hours, was cooled and then was removed of volatiles under reduced pressures to give 38 g. of yellow solids. These solids were taken up in 400 ml benzene, the organic phase was washed with 5×200 ml water and was dried (MgSO$_4$) and the benzene was removed under reduced pressures. The resulting yellow solid, after being washed with ether, yielded 16.5g (32% overall conversion) of the desired product, m.p. 140°–1°.

Calculated for $C_{10}H_{10}Cl_6N_2OS_4$: C, 23.3; H, 1.94; N, 5.44; Analyzed and found C, 23.4; H, 2.19; N, 5.43

EXAMPLE 27

Preparation of Dibutylthiocarbamoyl Oxazolidinothiocarbonyl Sulfide

To a solution of 37.4g (0.325 mole) of thiophosgene in 600 ml of ether was added a solution of 32.3g (0.25 mole) of dibutylamine and 25.3 g (0.25 mole) of triethylamine in 200 ml of ether at 0° over a period of 45 minutes. After stirring an additional one hour with no external cooling, the mixture was filtered and the resulting filtrate was removed of volatiles under reduced pressures. The last traces of thiophosgene were removed by treating the residual filtrate with 3 × 150 ml of hexane and distilling the volatiles under reduced pressures each time.

A solution of 41.5g (0.2 mole) of the above thiocarbamoyl chloride in 70 ml of methylene chloride was added to a solution of 50.2 g (0.2 mole) of triethylammonium 3-oxazolidinecarbodithioate in 200 ml of methylene chloride at 17°–20° in 30 minutes. After heating for one hour at 35°–40°, the mixture was filtered; the filtrate was evaporated under reduced pressures, and the residue was taken up in 300 ml of ether. After washing with 5 × 100 ml of 10% NaOH solution, the etheral solution was dried with Na$_2$SO$_4$, filtered, and removed of volatiles under reduced pressures to yield a soft orange-amber solid 50 g (78% conversion). Its infrared spectrum confirmed the desired structure.

Calculated for $C_{13}H_{24}N_2OS_3$: C, 48.7; H, 7.55; N, 8.74; Analyzed and found: C, 49.2; H, 7.51; N, 8.13

EXAMPLE 28

Preparation of Dibutylthiocarbamoyl (2-Trichloromethyloxazolidino)thiocarbonyl Sulfide To a solution of 22.4 (0.195 mole) of thiophosgene in 600 ml of ether was added a solution of 19.4g (0.15 mole) of dibutylamine and 15.2 g (0.15 mole) of triethylamine in 200 ml of ether at 0° in 45 minutes. After stirring an additional one hour with no external cooling, the mixture was filtered and the resulting filtrate was removed of volatiles at ambient temperatures at 1 mm Hg. To remove the last traces of thiophosgene from the crude thiocarbamoyl chloride, hexane (3 × 150 ml) was added to the residue and the volatiles removed under reduced pressures each time.

A solution of 28.6 g (0.138 mole) of the above chloride in 50 ml. of methylene chloride was added to a solution of 50.6g (0.138 mole) of triethylammonium 2-trichloromethyl-3-oxazolidinecarbodithioate in 200 ml of methylene chloride at 18°–22° in 20 minutes. After heating for one hour at 35°–40°, the mixture was filtered. The filtrate was distilled at ambient temperatures at 1 mm Hg to leave an amber liquid residue which was treated with 2 × 200 ml of ether and filtered each time to remove the solid triethylammonium chloride. The filtrate was taken up in 250 ml of ether and washed with 8 × 50 ml of 5% NaOH solution, followed by 8 × 100 ml of water. The etheral layer was dried with Na$_2$SO$_4$, filtered and removed of volatiles under reduced pressures to give a dark, amber liquid. This liquid was then washed with 10 × 150 ml ml of hexane to remove the turbidity and to yield an amber oil, 46g (76% conversion). Its infrared spectrum confirmed the desired structure.

Calculated for $C_{14}H_{23}Cl_3N_2OS_3$: N, 6.40; S, 21.9; Analyzed and found N, 5.99; S, 22.2

EXAMPLE 29

Preparation of Thiuram Disulfides from N-Carbodithioates of 2-Phenyloxazolidine and 2-Trichloromethyloxazolidine To a solution of 39.1g (0.12 mole) of triethylammonium (2-phenyl-3-oxazolidine)carbodithioate and 44.0g (0.12 mole) of triethylammonium (2-trichloromethyl-3-oxazolidine)carbodithioate in 3.5 liters of water and 200 ml of methanol was added to the solution of 28.7g (0.126 mole) of ammonium persulfate in 200 ml of water at 25° over a period of 10 minutes. The mixture was stirred an additional 15 minutes and then filtered. The resulting yellow solids, after being washed with 4 × 1 liter of water and dried in a vacuum desiccator for 5 days, weighed 53g (90% conversion), m.p. 70°–80°. The product is a mixture of bis (2-phenyloxazolidinothiocarbonyl) disulfide, bis(2-trichloromethyl oxazolidinothiocarbonyl) disulfide, and (2-phenyloxazolidino) thiocarbonyl[2-trichloromethyloxazolidino)-thiocarbonyl disulfide. Its infrared spectrum confirmed the expected structure.

Calculated for $C_{15}H_{15}Cl_3N_2O_2S_4$ (average): Cl, 21.7; N, 5.72; S, 26.1 Analyzed and found Cl, 21.3; N, 5.95; S, 26.2

EXAMPLE 30

Preparation of Bis[(5-phenyl-2-trichloromethyloxazolidino)thiocarbonyl] Disulfide A solution of 355.6g (3.56 moles) triethylamine, 203.6 g (2.68 moles) carbon disulfide, and 474 g (1.78 moles) 5-phenyl-2-trichloromethyloxazolidine (prepared from 2-amino-1-phenyl-ethanol and chloral; m.p. 67°–9°) was stirred for nine days at ambient temperatures. The solution was removed of volatiles under reduced pressures to leave a residual viscous oil which was extracted with ethyl ether (10 × 200 ml). The combined ether extracts were removed of solvent under reduced pressures to yield 330 g of the crude, liquid triethylammonium 5-phenyl-2-trichloromethyl-3-oxazolidinecarbodithioate.

To 251 g (0.566 mole) of the above triethylammonium salt in two liters of water was added a solution of 64.6 g (0.283 mole) of ammonium persulfate in 90 ml of water at 25° over a period of 10 minutes. The resulting tan solids were filtered, washed with water, and then taken up in isopropanol. Water was slowly added to reprecipitate the tan product which, after having been dried in a vacuum desiccator over NaOH, weighed 12.5g (7% conversion), m.p. 89°–93°. Its infrared spectrum is consistent with the desired structure.

Calculated for $C_{20}H_{18}Cl_6N_2O_2S_4$: Cl, 32.3; N, 4.25; S, 19.4; Analyzed and found Cl, 31.7; N, 4.38; S, 19.2;

EXAMPLE 31

Preparation of Bis[(2,2-dimethyloxazolidino)thiocarbonyl]Disulfide

To a cold (−10°) solution of 202 g (2.0 moles) of triethylamine and 360 g (1.27 moles) of 2,2-dimethyloxazolidine [(prepared by the method of E. Bergman, J.A.C.S. 75, 358 (1953)] in one liter of ether was added 152g (2.0 moles) of carbon disulfide over a period of 15 minutes. Solids formed during the additional one hour of stirring at −10° to 6°. The mixture was then filtered; the solids were washed with 2 × 250 ml of ether and were air-dried for 20 minutes to obtain 347g of the pale yellow, solid triethylammonium bis (2,2-dimethyl-3-oxazolidine carbodithioate).

A solution of 91.2 g (0.40 mole) of ammonium persulfate in 200 ml of water was added to a solution of 220.9 g (0.80 mole) of the above triethylammonium salt at 5°–9° in 20 minutes. After being stirred at 5°–10° for an additional 20 minutes, the mixture was filtered and the solid was washed with 3 × 500 ml of water. The solid was extracted with 3 × 500 ml of ether; the combined extracts were dried, filtered, and evaporated of volatiles at 25° and 1 m Hg to yield, after washing with 500 ml of hexane and drying, 43 g (31% conversion, based on the 2,2-dimethyloxazolidine) of a cream-colored solid product, m.p. 86°–7°. Its infrared spectrum confirmed the desired structure.

Calculated for $C_{12}H_{20}N_2O_2S_4$: C, 40.9; H, 5.72; N, 7.95; S, 36.3 Analyzed and found C, 40.4; H, 5.55; N, 7.76; S, 37.1

EXAMPLE 32

Preparation of Bis{[2-(1-ethylpentyl)oxazolidino]thiocarbonyl} Disulfide

To a solution of 117 g (1.16 moles) of triethylamine and 133 g (0.77 mole) of 2-(1-ethylpentyl)oxazolidine [containing mainly the tautomer, N-α-ethylpentylidene-2-hydroxyethylamine, and prepared according to A. Cope, J.A.C.S. 64, 1503 (1942)] in one liter of ether was added 88 g (1.16 moles) of carbon disulfide at 10°–20° over a period of 35 minutes. Stirring was continued for 17 hours at ambient temperatures. Solids (13 g of triethylammonium N-(2-hydroxyethyl)dithiocarbamate were filtered off and the resulting filtrate was removed of volatiles at 25°/150 mm Hg to give 242g of crude triethylammonium 2-(1-ethylpentyl)-3-oxazolidinecarbodithioate.

To 69.2 g (0.2 mole) of the above triethylammonium salt in 700 ml of water was added a solution of 25.1 g (0.11 mole) of ammonium persulfate in 250 ml of water at 5°–10° over a period of 35 minutes. Stirring was continued for an additional 10 minutes and then 150 ml of methylene chloride was added to take up the oil that had formed. The entire mixture was transferred to a separatory funnel; the organic layer was separated, washed with 3 × 150 ml of water, dried with MgSO$_4$, filtered, and removed of volatiles at ambient temperatures and 1 mm Hg to yield 33 g (60% conversion based on the oxazolidine) of viscous, yellow, liquid product. Its infrared spectrum confirmed the expected structure.

Calculated for $C_{22}H_{40}N_2O_2S_4$: C, 53.6; H, 8.12; N, 5.69 Analyzed and found C, 53.9; H, 8.52; N, 5.56

EXAMPLE 33

Preparation of Bis{[2-(1-ethyl-1-pentenyl)oxazolidino]thiocarbonyl} Disulfide

A solution of 77.8 g (0.77 mole) of triethylamine 58.5 g (0.77 mole) of carbon disulfide, and 59 g (0.51 mole) of crude 2-(1-ethyl1-pentenyl)oxazolidine (b.p. 85°–8°/0-.6–1 mm Hg prepared from ethanolamine and 2-ethyl-2-hexenal by azeotroping with benzene; distilled and used immediately) was stirred for 72 hours. After having removed the the volatiles at RT/1 mm Hg the resulting red liquid was treated with ether and stirred. The filtrate was evaporated under reduced pressures to remove the ether. The residual red liquid was then treated with 1.5 liters of water and the mixture was filtered through Microcel (absorbs viscous, red oil).

To the above filtrate, containing triethylammonium 2-(1-ethyl-1-pentenyl)-3-oxazolidinecarbodithioate was added 31.4 g (0.137 mole) of ammonium persulfate in 200 ml. of water at 20°–5° C. over a period of 15 minutes. The aqueous layer was decanted to leave as a residue a yellow, viscous oil which was taken up in 300 ml of ether. The etheral layer was washed with 2 × 200 ml of water, dried with MgSO$_4$, and filtered. The filtrate was evaporated at ambient temperatures and 1 mm Hg to yield as residue 17 g (10% conversion based on the substituted)oxazolidine) of yellow, viscous product. Its infrared spectrum confirmed the expected structure.

Calculated for $C_{22}H_{36}N_2O_2S_4$: C. 54.1; H, 7.43; N, 5.74; S. 26.2 Analyzed and found C, 53.6 H, 7.54; N, 5.87; S, 25.6

EXAMPLE 34

Preparation of Bis[(2-Methyl-2-phenyloxazolidine)thiocarbonyl]Disulfide

A solution of 412 g (4.06 moles) of triethylamine, 310 g (4.06 moles) of carbon disulfide, and 440 g of crude 2-methyl-2-phenyloxazolidine [obtained from 2 moles acetophenone and ethanolamine and containing mainly the tautmer N-α-methylbenzylidene-2-hydroxyethylamine, see L. Daashi et al., J.A.C.S. 77, 3673 (1950)] was stirred for 11 hours, during which time two liquid phases were formed. The mixture was removed of volatiles at 25°/1 mm Hg. The resulting viscous, red liquid was treated with a solution of 5000 ml water and 500 ml ispropanol, then filtered through a pad of Microcel which absorbed the thick, immiscible oil. To the red filtrate of ca. 5500 cc. transferred to a 12 liter flask, was added a solution of 248 g (1.09 moles) of ammonium persulfate in one liter of water at ambient temperatures over a period of 30 minutes. The yellow-solids which floated to the top were decanted, filtered and washed twice in a Waring Blendor to yield 180 g crude product which was treated with 10 × 200 ml 95% ethanol.. Two liters of water were slowly added to the combined ethanol extracts to yield, after filtering and drying over NaOH in a vacuum desiccator, 26 g (5.5% conversion based on acetophenone) of bright yellow solid product. m.p. 86°–90°. Its infrared spectrum confirmed the expected structure.

Calculated for $C_{22}H_{24}N_2O_2S_4$: N, 5.88 Analyzed and found N, 5.80

EXAMPLE 35

Preparation of Bis[(2-p-chlorophenyloxazolidino)thiocarbonyl]Disulfide

To a solution of 97.3 g (0.27 mole) of triethylammonium 2-p-chlorophenyl-3-oxazolidinecarbodithioate (white solid m.p. 74°–6°, prepared from 2-p-chlorophenyloxazolidine, triethylamine and carbon disulfide in ether) in two liters water and 150 ml methanol was added a solution of 30.7 g (0.135 mole) of ammonium persulfate at 15°–19° over a period of 20 minutes. The mixture was stirred an additional 15 minutes and then was filtered. The white solids (after having been washed with 5 × 500 ml water in a Waring Blendor) were taken up in 1.2 liters methylene chloride. The very wet organic solution was dried several times with $MgSO_4$, filtered, and flash-evaporated of volatiles at 25°/1 mm Hg to give a greenish-yellow oil. Ether (600 ml) was added with rapid stirring to precipitate a white solid product, which after filtering and drying, weighed 45 g (64% conversion), M.P. 180°–2°. Its infrared spectrum confirmed the expected structure.

Calculated for $C_{20}H_{18}Cl_2N_2O_2S_4$: Cl, 13.7; N, 5.42; Analyzed and found Cl, 13.7; N, 5.72

EXAMPLE 36

Preparation of Bis{[(2-p-dimethylaminophenyl)oxazolidino]thiocarbonyl} Disulfide To a solution of 101 g (1.0 mole) of triethylamine and 95.5 g (0.5 mole) of 2-(p-dimethylaminophenyl)oxazolidine[prepared by a procedure of Nakamichi, J. Org. C. 22 159 (1957) from ethanolamine and p-dimethylaminobenzaldehyde] in 500 ml of tetrahydrofuran was added 76 g (1.0 mole) of carbon disulfide in 10 min. at 21°–2°. The reaction mixture was stirred for three additional hours, during which time solids formed, and then let stand at ambient temperatures overnight. The mixture was filtered; the solid was returned to the flask and stirred with 500 ml of tetrahydrofuran; the mixture was again filtered; and the solid after washing with an additional 200 ml of tetrahydrofuran, was immediately transferred into a vacuum desiccator and was dried at 25°/1 mm Hg. A white solid, 161 g. was obtained, m.p. 101°–4° (decomposition with gas evolution).

A solution of 22.8 g (0.1 mole of ammonium persulfate in 200 ml of water was added over a period of 20 min. to 73.8 g (0.2 mole) of the above triethylammonium salt in 3.5 liters of water at 5°–6°. After stirring an additional 15 min., the very fine solids were taken up in 10 × 200 ml of ether and the resulting etheral solution was separated from the aqueous phase and was then removed of volatiles at ambient temperatures/1 mm Hg. The resulting semi-solid product was triturated with 350 ml of isopropanol to yield after drying in a vacuum desiccator, 24 g (39% conversion, based on the substituted oxazolidine) of yellow solid product, m.p. 81°–90° (dec.). Its infrared spectrum confirmed the desired structure.

Calcuated for $C_{21}H_{30}N_4O_2S_4$: C. 53.9; H, 5.61; N, 10.5; S, 23.9 Analyzed and found C, 54.5; H, 5.99; N, 9.90; S, 22.3

EXAMPLE 37

Preparation of Morpholinothiocarbonyl (2-Trichloromethyloxazolidino)thiocarbonyl Sulfide At 10°–20° C. with rapid stirring in a nitrogen-filled reflux system a solution of 21.8 g (0.25 mole) morpholine and 25.3 g (0.25 mole) triethylamine in 250 ml anhydrous ethyl ether was added dropwise to a solution of 40.0 g (0.313 mole) thiophosgene in 600 ml anhydrous ethyl ether. The resulting triethylammonium chloride was filtered off and washed on the filter with 100 ml anhydrous ether. The combined filtrates were stripped at reduced pressure at room temperature. The oily residue was twice treated with 150 ml hexane and vacuum stripped. The resulting slurry of morpholinothiocarbamyl chloride weighed 32.9 g.

The above 32.9 g (0.1987 mole) morpholinothiocarbamyl chloride was dissolved in 75 ml methylene chloride and refluxed for 2 hours with a solution of 73.1 g (0.198 mole) triethylammonium 2-trichloromethyl-3-oxazolidinecarbodithioate in 300 ml methylene chloride. At room temperture, 200 ml water was stirred in. The organic layer (bottom) was separated and washed five times with 100 ml portions of 10% aqueous sodium hydroxide, once with 100 ml of 1% sulfuric acid, then twice 100 ml portions of water until the wash was neutral to pH paper. The organic layer was dried with anhydrous magnesium sulfate, filtered and the filtrate was vacuum-stripped to leave 71.2 g of oily residue. The residue was washed with hexane to give a sticky solid which was treated with 550 ml hot 95% ethanol. The hot suspension was cooled to 10° C. and filtered to give 37.9 g of product, m. 107°–118° C. Concentration of the filtrate to half volume gave 3.4 g of additional product which was added to the first crop and dried in a vacuum desiccator to give 32.6 g (41% yield based on the carbodithioate). An analytical sample was prepared by extraction of the product with hot 95% ethanol, followed by cooling and filtering of the extract to recover the solid product, raised the melting point to 121°–127° C. Washing the product with boiling hexane resulted in a m.p. 124°–128° C. Its infrared spectrum confirmed the desired structure.

Calculated for $C_{10}H_{13}Cl_3N_2O_2S_3$: C, 30.34; H, 3.29; N, 7.08; Analyzed and found C, 30.70; H, 3.55; N, 6.48

EXAMPLE 38

Bis(pentamethylene)Thiuram Disulfide

The above compound was prepared by the method of E. Blake, Journal American Chemical Society 65 1267 (1943).

EXAMPLE 39

Mixture of Thiuram Disulfides from N-Carbothioates of Diethylamine and Dimethylamine.

This is a commercial product known as Pennac® TM or Methyl Ethyl Tuads® available from Pennwalt Corporation or R. T. Vanderbilt Co., respectively, and is disclosed as a blend of tetraethylthiuram disulfide and tetramethylthiuram disulfide.

EXAMPLE 40

Preparation of Di(n-octyl)thiocarbamoyl-2-(Trichloromethyloxazolidino)thiocarbonyl Sulfide To 75.8 g (0.65 mole) thiophosgene in one liter of ethyl ether at 0° C. was added a solution of 95.3 g (0.5 mole) 2-trichloromethyloxolidine, 50.5 g (0.5 mole) triethylamine and 350 ml. ethyl ether over a 40 minute period. After stirring an additional two hours with no external cooling, the mixture was filtered; the filtrate was evaporated to dryness under reduced pressures and the resulting residue was extracted with 5×200 ml. of hexane. The combined extracts were removed of solvent to yield 89 g of 2 trichloromethyloxazolidinothiocarbamoyl chloride.

To a sodium di-n-octyldithiocarbamate solution, prepared from 36.2 g (0.15 mole) di-n-octylamine, 12 g (0.157 mole) carbon disulfide 12.4 g (0.153 mole) of 50% aqueous sodium hydroxide, 200 ml water and 400 ml tetrahydrofuran, was added at 25° a solution of 40.5 g (0.15 mole) of the above thiocarbamoyl chloride over a 20 minute period. After stirring an additional 23 hours, the mixture was filtered and the resulting filtrate was evaporated under reduced pressures at ambient temperatures to remove a major portion of the solvents. The residual was washed with 10×100 ml. of water, dried, and filtered. The filtrate was evaporated under reduced pressures to yield a residual amber oil (74.5 g., 90% conversion based on the thiocarbamoyl chloride) representing the desired product.

Calculated for: $C_{22}H_{39}Cl_3N_2OS_2$: C, 48.3; H, 7.08; Cl, 19.8; N, 4.97; S, 17 Analyzed and found C, 4.0; H, 7.15; Cl 19.4; N, 5.09; S, 17

The above compounds were each used in the following vulcanization recipe for EPDM elastomers wherein amounts are based on parts by weight per hundred parts of elastomer.

| EPDM Elastomer Composition | Parts |
| --- | --- |
| Ethylene-propylene-diene terpolymer | 100 |
| Napthenic oil | 50 |
| Carbon Black | 100 |
| Zinc Oxide | 5 |
| 2-Mercaptobenzothiazole | 0.5 |
| Stearic acid | 2 |
| Sulfur | 0.5 |
| Accelerator | 2 |

The curing of the above vulcanization composition was carried out at 320° F., removing samples at 10, 30 and 60 minute intervals for testing. The physical data for the various vulcanizates each containing a different accelerator identified by the example number under which their preparation is shown, are presented in Table 1 below.

TABLE I

| Example and Accelerator No. | Bloom | Tensile (psi) at cure time (minutes) | | | Modulus, 300% (psi) at cure time (minutes) | | |
| --- | --- | --- | --- | --- | --- | --- | --- |
| | | 10 | 30 | 60 | 10 | 30 | 60 |
| 1 | Bl | 1840 | 2590 | 2640 | 1100 | 1930 | 2360 |
| 2 | Bl | 1550 | 2575 | 2655 | 2000 | 1625 | 925 |
| 3 | Bl | 2300 | 2625 | 2650 | 1600 | 2425 | — |
| 4 | Bl | 2200 | 2625 | 2475 | 1525 | 2425 | 2475 |
| 5 | Bl | 2090 | 2600 | 2700 | 1500 | 2210 | 2500 |
| 6 | Bl | 2000 | 2300 | 2400 | 1300 | 2025 | 2250 |
| 7 | Bl | 2010 | 2700 | 2750 | 1400 | 2150 | 2400 |
| 8 | Bl | 2300 | 2325 | 2425 | 1600 | 2150 | 2325 |
| 9 | Bl | 2225 | 2575 | 2575 | 1700 | 2200 | 2450 |
| 10 | Bl | 2225 | 2425 | 2425 | 1600 | 1975 | 2100 |
| 11 | Nb | 2400 | 2450 | 2525 | 1850 | — | — |
| 12 | Nb | 2400 | 2700 | 2850 | 1775 | 2625 | — |
| 13 | Nb | 2260 | 2570 | 2400 | 1590 | 2300 | — |
| 14 | Nb | 2360 | 2500 | 2460 | 1600 | 2320 | 2460 |
| 15 | Nb | 2300 | 2350 | 2425 | 1715 | 2000 | — |
| 16 | Nb | 2350 | 2600 | 2625 | 1625 | 2350 | — |
| 17 | Nb | 2200 | 2480 | 2400 | 1640 | 2320 | 2400 |
| 18 | Nb | 2340 | 2610 | 2700 | 1700 | 2390 | 2600 |
| 19 | Nb | 2025 | 2600 | 2600 | 1375 | 2100 | 2500 |
| 20 | Nb | 1990 | 2450 | 2460 | 1250 | 1910 | 2250 |
| 21 | Nb | 1520 | 2240 | 2340 | 980 | 1710 | 2150 |
| 22 | Nb | 2370 | 2450 | 2550 | 1790 | 2390 | — |
| 23 | Nb | 2060 | 2450 | 2610 | 1370 | 2140 | 2450 |
| 24 | Nb | 1670 | 2340 | 2420 | 1110 | 1820 | 2250 |
| 25 | Nb | 1650 | 2310 | 2310 | 2000 | 1770 | 1060 |
| 26 | Nb | 1700 | 2200 | 2370 | 1060 | 1850 | 2120 |
| 27 | Nb | 1830 | 2650 | 2660 | 1050 | 1820 | 2210 |
| 28 | Nb | 2080 | 2620 | 2800 | 1200 | 2000 | 2410 |
| 29 | Nb | 2450 | 2600 | 2660 | 1540 | 2390 | 2600 |
| 30 | Nb | 2400 | 2620 | 2790 | 1420 | 2300 | 2580 |
| 31 | Nb | 490 | 1320 | 1900 | 300 | 820 | 1180 |
| 32 | Nb | 590 | 1430 | 2060 | 390 | 900 | 1310 |
| 33 | Nb | 1900 | 2600 | 2720 | 1070 | 1700 | 2200 |
| 34 | Nb | 1890 | 2690 | 2790 | 1100 | 1900 | 2420 |
| 35 | Nb | 2170 | 2700 | 2670 | 1310 | 2140 | 2300 |
| 36 | Nb | 610 | 1380 | 1990 | 400 | 900 | 1270 |
| 37 | Nb | 2270 | 2720 | 2800 | 1400 | 2200 | 2450 |
| 38 | Bl | 1600 | 2610 | 2800 | 950 | 1670 | 2220 |
| 39 | Bl | 1850 | 2490 | 2610 | 1210 | 2000 | 2380 |
| 40 | Nb | 610 | 2010 | 2000 | 400 | 1240 | 1400 |

*Bl=Bloom; Nb=No Bloom

The above results are surprising in view of the bloom causing, known thiuram sulfides not containing the oxazolidine or thiazolidine moiety of Examples 1, 2, 38 and 39 (see Table 1). Furthermore, the non-blooming characteristics of the claimed thiurams are also surprising in view of the bloom caused by the new asymmetrical thiuram sulfides of Examples 4, 6, and 7 in which one of the nitrogen-atoms is not part of an oxazolidine or thiazolidine ring and is substituted with alkyls the carbon atoms of which total less than 5, and in view of the bloom caused by the new mixtures of thiuram disulfides of Examples 3 and 5 which, on molar basis, contain predominently a blend of symmetrical oxazolidine or thiazolidine derived thiuram disulfides, respectively, with asymmetrical thiuram disulfides in which one of the nitrogen atoms is not part of an oxazolidine or thiazolidine ring but is substituted with alkyls, the carbon atoms of which total less than 5. However, the asymmetrical compounds of Examples 21, 24, 26, 27 and 37 and the mixtures of Examples 19, 20, 22, and 29 containing asymmetrical thiuram disulfides in which one of the nitrogen atoms is not part of an oxazolidine or thiazolidine ring but is substituted with alkyls, the carbon atoms of which total more than 5, were not only non-blooming but also fast-acting. The non-blooming effect of the subject thiuram is unexpected also considering the fact the the products containing two unsubstituted oxazolidine rings as shown in Examples 8, 9, and 10 cause blooming. In view of the non-blooming accelerators of Examples 11-37 the similar products of Examples 3, 4, 5, 6, 7 and especially Examples 8, 9, and 10 might be expected to be non-blooming, too, but surprisingly they caused blooming.

What is claimed is:

1. In a method of curing ethylene-propylenediene elastomers wherein the elastomer composition has sulfur and/or sulfur donor vulcanization accelerator and other rubber compound ingredients admixed therewith, and said elastomer composition is cured at elevated temperature, the improvement which comprises using as the vulcanization accelerator a compound having the following general structure:

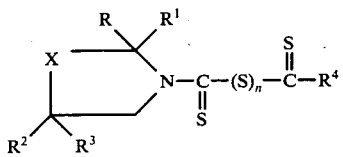

wherein R, $R^1$, $R^2$ and $R^3$ are independently selected from the group consisting of hydrogen, alkyl, and chloroalkyl radicals each having from 1 to 17 carbon atoms, alkenyl radicals having from 2 to 17 carbon atoms, phenyl naphthyl, substituted phenyl and substituted naphthyl radicals each having substituents selected from the group consisting of Cl, —OH, $OR^5$ and —$NR^5R^6$ wherein $R^5$ and $R^6$ are alkyl radicals having 1 to 8 carbon atoms, and n is an integer of from 1 to 4; $R^4$ is selected from the group consisting of a) —$NR^7R^8$ wherein $R^7$ and $R^8$ are independently selected from alkyl radicals having from 1 to 18 carbon atoms and together having a total of at least 5 carbon atoms, b) -NZ wherein N is the ring nitrogen atom of a cyclic amine and Z represents that portion of the cyclic amine ring having at least 5 ring carbon atoms one of which can be replaced by oxygen or sulfur, and c)

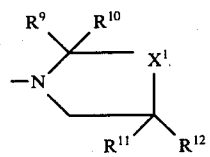

wherein $R^9$, $R^{10}$, $R^{11}$ and $R^{12}$ are independently selected from the same group from which R is selected and at least one of $R^9$, $R^{10}$, $R^{11}$ and $R^{12}$ is other than hydrogen; and X and $X^1$ are independently selected from oxygen and sulfur atoms.

2. The method of claim 1 wherein X is oxygen.
3. The method of claim 1 wherein X is sulfur.
4. The method of claim 1 wherein $R^4$ is —$NR^7R^8$.
5. The method of claim 4 wherein $R^7$ and $R^8$ are butyl radicals.
6. The method of claim 4 wherein $R^7$ and $R^8$ are octyl radicals.
7. The method of claim 1 wherein $R^4$ is —NZ.
8. The method of claim 7 wherein —NZ represents a morpholino radical.
9. The method of claim 8 wherein X is oxygen, R is —$CCl_3$, and $R^1$, $R^2$ and $R^3$ are hydrogen.
10. The method of claim 1 wherein $R^4$ is

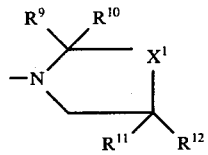

11. The method of claim 10 wherein $X^1$ is oxygen.
12. The method of claim 11 wherein X is oxygen, R is —$CCl_3$, $R^9$ is phenyl and $R^1$, $R^2$, $R^3$, $R^{10}$, $R^{11}$ and $R^{12}$ are hydrogen.
13. The method of claim 11 wherein X is oxygen, R and $R^9$ are —$CCl_3$, $R^2$ and $R^{11}$ are phenyl and $R^1$, $R^3$, $R^{10}$ and $R^{12}$ are hydrogen.
14. The method of claim 10 wherein $X^1$ is sulfur.
15. The method of claim 10 wherein R and $R^9$ are —$CCl_3$, and $R^1$, $R^2$, $R^3$, $R^{10}$, $R^{11}$ and $R^{12}$ are hydrogen.
16. The method of claim 15 wherein X and $X^1$ are both oxygen.
17. The method of claim 16 wherein n is 2.
18. The method of claim 16 wherein n is 1.
19. The method of claim 15 wherein X and $X^1$ are both sulfur.
20. The method of claim 15 wherein X is oxygen and $X^1$ is sulfur.
21. The method of claim 10 wherein R and $R^9$ are phenyl and $R^1$, $R^2$, $R^3$, $R^{10}$, $R^{11}$ and $R^{12}$ are hydrogen.
22. The method of claim 10 wherein said accelerator comprises a mixture of two compounds each having the general structure of claim 34 wwherein n is 2, X and $X^1$ are oxygen, $R^1$, $R^2$, $R^3$, $R^{10}$, $R^{11}$ and $R^{12}$ are hydrogen, and in one of said compounds, R and $R^9$ are —$CCl_3$ and in the other of said compounds R and $R^9$ are phenyl.
23. The method of claim 1 wherein said accelerator comprises a mixture of two compounds each as described in claim 26 wherein n=2, and in one of said compounds $R^4$ is $NR^7R^8$ and in the other of said compounds $R^4$ is

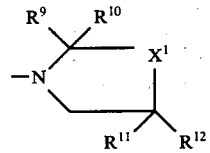

24. The method of claim 23 wherein $X^1$ is oxygen.
25. The method of claim 1 wherein R is —$CCl_3$, and $R^1$, $R^2$ and $R^3$ are hydrogen.

* * * * *